United States Patent [19]

Zinnes et al.

[11] 3,931,229

[45] Jan. 6, 1976

[54] 3-THIOMETHYL-2[2-(DIALKYLAMINO)E-THYL]INDOLES

[75] Inventors: Harold Zinnes, Rockaway; Martin L. Schwartz, Gillette, both of N.J.

[73] Assignee: Warner-Lambert Company, Morris Plains, N.J.

[22] Filed: Apr. 8, 1974

[21] Appl. No.: 458,916

Related U.S. Application Data

[63] Continuation-in-part of Ser. No. 391,171, Aug. 23, 1973, abandoned.

[52] U.S. Cl............ 260/326.12 R; 260/306.7 R; 260/309.6
[51] Int. Cl.².................................. C07D 209/04
[58] Field of Search............ 260/326.12 R, 306.7 R

[56] References Cited
UNITED STATES PATENTS 3,033,875  5/1962  Nutting et al............. 260/326.12 R
3,478,051  11/1969  Houlihan et al.......... 260/326.12 R Primary Examiner—Richard J. Gallagher
Assistant Examiner—James H. Turnipseed
Attorney, Agent, or Firm—Albert H. Graddis; Frank S. Chow

[57] ABSTRACT

3-Thiomethyl-2[2-(dialkylamino)ethyl]indoles having the following structural formula are disclosed

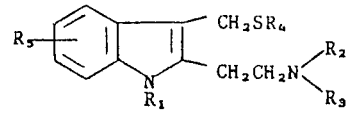

I

In the above formula, $R_1$, $R_2$, and $R_3$ are hydrogen or alkyl, $R_4$ is alkyl, aryl, aralkyl, or a heterocyclic, $R_5$ is hydrogen, alkyl, halogen, alkoxy, hydroxyl and the like.

These compounds exhibit central nervous system depressing properties and are useful as anti-aggression agents.

22 Claims, No Drawings

3,931,229

3-THIOMETHYL-2[2-(DIALKYLAMINO)ETHYL-]INDOLES

This application is a continuation-in-part of our copending application Ser. No. 391,171 filed Aug. 23, 1973 now abandoned.

The present invention relates to 3-THIOMETHYL-2[2-(DIALKYLAMINO)ETHYL]INDOLES having the structural formula

[Structure I: indole with $R_5$ on benzene ring, $CH_2SR_4$ at 3-position, $CH_2CH_2N(R_2)(R_3)$ at 2-position, $R_1$ on N]

wherein $R_1$, $R_2$, and $R_3$ are hydrogen or alkyl, $R_4$ is alkyl, aryl, aralkyl, or a heterocyclic, $R_5$ is hydrogen, alkyl, halogen, alkoxy and hydroxyl and the like.

In the above definitions for $R_1$, $R_2$, $R_3$, $R_4$ and $R_5$ "alkyl" and "alkoxy" are meant to have 1 to 7 carbon atoms in the carbon chain. It includes straight chain as well as branched chain radicals. The term includes for example methyl, ethyl propyl, isopropyl and the like. The term "aryl" denotes a monocyclic aromatic hydrocarbon preferably of 6 to 10 carbon atoms for example phenyl, tolyl, and the like. The term "aralkyl" encompasses an alkyl group as defined, in which a hydrogen atom is substituted by "aryl" such as benzyl, phenethyl and the like. The aryl portion may be substituted, e.g., chloro, amino or unsubstituted. The term heterocyclic denotes a 5 or 6-membered hetero ring having at least one hetero atom in the ring which may be either nitrogen, oxygen or sulfur. Representative heterocyclics are, for example, pyridyl, thienyl, furyl, thiazolyl, imidazolyl and the like.

According to the present invention the above compounds are prepared by treating the quaternary salt of 1,2,3,4-tetrahydro-$\gamma$-carboline of structure II with the salt of a thiol of structure III to give compound I. This reaction is illustrated by the scheme:

[Scheme: quaternary salt II + $R_4S^\ominus Na^\oplus$ (III) → I]

II    III

The starting 1,2,3,4-tetrahydro-$\gamma$-carbolines are prepared by procedures known to the art (See V. Boekelheide, et al/JACS, 72, 2132 (1950), C. J. Cattanach, et al/J. Chem. Soc. (C) 1235 (1968)). They are readily converted to the corresponding quaternary salts by treatment of the free base with alkyl halide.

A more detailed description of this process is given below under "General Procedure."

The compounds of this invention form salts with pharmaceutically acceptable acids and these salts are included within the scope of this invention. These salts include, for example, salts formed with hydrochloric, sulfuric, nitric, acetic acids and the like.

The above compounds and their salts exhibit central nervous system depressing activity. For example, when administered intraperitonially to rodents such as mice at a dose of 10–100 mg/kg, sedation of the mice is produced. Additionally, the compounds of this invention when evaluated in other animal models, e.g. isolated fighting mice and killer rats, was found to reduce aggression.

These compounds are useful as mild sedatives or anti-aggression agents, within the above described dose range.

In order to use these compounds, they are formulated with tablets or injections utilizing known excipients such as lactose or sterile water by methods well known to the pharmacist's art.

To further illustrate the practice of this invention, the following examples are included:

EXAMPLE 1

3-Thiomethyl-2[2-(dialkylamino)ethyl]indoles — General Procedure.

A mixture of 0.07 mol of an appropriate 2-alkyl-1,2,3,4-tetrahydro-$\gamma$-carboline quaternary salt, 0.077 mol of an appropriate thiol derivative, 70 ml of 1.0 N sodium hydroxide, and 100 ml of water was refluxed with stirring for three hours and allowed to cool to 25°. The crude product separated out as a crystalline precipitate or as a gummy semi-solid. Two work-up procedures were employed.

Method A

In those cases where a crystalline precipitate formed, it was collected, washed well with water, and recrystallized as described in the individual examples.

Method B

When a semi-solid was obtained, it was separated from the aqueous solution by decantation of the latter and was dissolved in ether. When an oil was obtained, the mixture was extracted with ether. The ether solution was washed successively with 1N sodium hydroxide, water, and saturated aqueous sodium chloride solution. It was then dried and evaporated to give a residue which was purified as described in the individual examples.

EXAMPLE 2

[Structure: indole with $CH_2SC_2H_5$ at 3-position and $CH_2CH_2N(CH_3)_2$ at 2-position, NH]

2[2-(Dimethylamino)ethyl]-3-[(ethylthio)methyl]indole

The reaction was carried out with 2-methyl-1,2,3,4-tetrahydro-$\gamma$-carboline methiodide and ethanethiol, using Method A for the workup. Recrystallization from 50 ml of ethyl acetate gave 8.9 g of product; mp 59°–61°.

Anal. Calcd for $C_{15}H_{22}N_2S$: C, 68.66; H, 8.45; N, 10.67; S, 12.22.

Found: C, 68.90; H, 8.42; N, 10.47; S, 12.47.

EXAMPLE 3

[Structure: indole with $CH_2SC_6H_5$ at 3-position and $CH_2CH_2N(CH_3)_2$ at 2-position, NH]

2-[2-(Dimethylamino)ethyl]-3-[(phenylthio)methyl]indole

The reaction was carried out with 2-methyl-1,2,3,4-tetrahydro-γ-carboline methiodide and thiophenol, using Method B for the workup. Recrystallization from 100 ml of isopropyl ether gave 14.9 g of product; mp 97°–99°.

Anal. Calcd for $C_{19}H_{22}N_2S$: C, 73.51; H, 7.14; N, 9.02; S, 10.33.

Found: C, 73.74; H, 7.34; N, 8.96; S, 10.21.

EXAMPLE 4

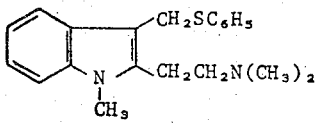

1-Methyl-2-[2-(Dimethylamino)ethyl]-3-[(phenylthio) methyl]indole

The reaction was carried out with 2,5-dimethyl-1,2,3,4-tetrahydro-γ-carboline methiodide and thiophenol, using work-up Method B. Recrystallization from 60 ml of hexane gave 11.2 g of product; mp 58°–60°.

Anal. Calcd for $C_{20}H_{24}N_2S$: C, 74.03; H, 7.46; N, 8.03; S, 9.88.

Found: C, 74.11; H, 7.54; N, 8.43; S, 9.93.

EXAMPLE 5

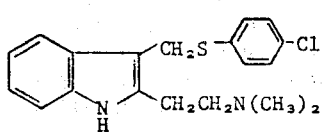

2-[2-(Dimethylamino)ethyl]-3-[(p-chlorophenylthio)methyl]indole

The reaction was carried out with 2-methyl-1,2,3,4-tetrahydro-γ-carboline methiodide and p-chlorothiophenol, using work-up Method B. Recrystallization from 500 ml of isopropyl ether gave 15 g of product; mp 115°–117°.

Anal. Calcd for $C_{19}H_{21}ClN_2S$: C, 66.17; H, 6.14; Cl, 10.28; N, 8.12; S, 9.30.

Found: C, 66.00; H, 5.89; Cl, 10.16; N, 8.09; S, 9.13.

EXAMPLE 6

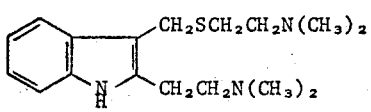

2-[2-(Dimethylamino)ethyl]-3-[2-(dimethylamino)ethylthiomethyl]-indole

The reaction was carried out with 2-methyl-1,2,3,4-tetrahydro-γ-carboline methiodide and 2-dimethylaminoethanethiol, using work-up Method B. Recrystallization from 60 ml of hexane gave 10.4 g of product; mp 52°–54°.

Anal. Calcd for $C_{17}H_{27}N_3S$: C, 66.84; H, 8.91; N, 13.75; S, 10.50.

Found: C, 66.77; H, 8.97; N, 13.59; S, 10.59.

EXAMPLE 7

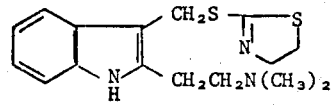

2-[2-(Dimethylamino)ethyl]-3-[(2-thiazolin-2-ylthio)methyl]indole

The reaction was carried out with 2-methyl-1,2,3,4-tetrahydro-γ-carboline methiodide and 2-mercapto-2-thiazoline, using workup Method A. Recrystallization from 140 ml of ethyl acetate gave 14.5 g of product; mp 140°–143°.

Anal. Calcd for $C_{16}H_{21}N_3S_2$: C, 60.15; H, 6.63; N, 13.15; S, 20.07.

Found: C, 59.89; H, 6.68; N, 13.14; S, 20.04.

EXAMPLE 8

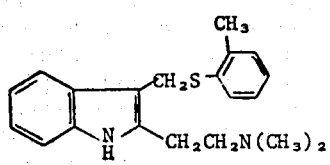

2-[2-(Dimethylamino)ethyl]-3-[(o-tolylthio)methyl]indole

The reaction was carried out with 2-methyl-1,2,3,4-tetrahydro-γ-carboline methiodide and o-thiocresol, using work-up Method B. Recrystallilzation from 150 ml of cyclohexane gave 11.1 g of product; mp 134°–137°.

Anal. Calcd for $C_{20}H_{24}N_2S$: C, 74.03; H, 7.46; N, 8.63; S, 9.88.

Found: C, 74.13; H, 7.76; N, 8.76; S, 9.89.

EXAMPLE 9

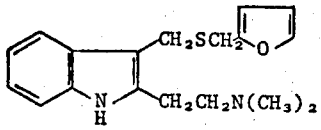

2-[2-(Dimethylamino)ethyl]-3-[(2-furylmethylthio)methyl]indole

The reaction was carried out with 2-methyl-1,2,3,4-tetrahydro-γ-carboline methiodide and 2-furylmethylthiol, using work-up Method B. Recrystallization from 100 ml of isopropyl ether gave 15.5 g of product; mp 79°–82°.

Anal. Calcd for $C_{18}H_{22}N_2OS$: C, 68.75; H, 7.05; N, 8.91; S, 10.20.

Found: C, 68.92; H, 7.19; N, 8.91; S, 10.47.

EXAMPLE 10

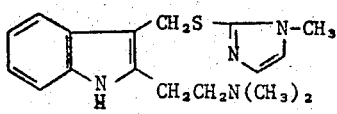

2-[2-(Dimethylamino)ethyl]-3-[(1-methylimidazol-2-ylthio) methyl]indole

The reaction was carried out with 2-methyl-1,2,3,4-tetrahydro-γ-carboline methiodide and 2-mercapto-1-methylimidazole. Work-up Method B was used with the exception that ethyl acetate was used to dissolve the crude gum instead of ether. Recrystallization from 175 ml of isopropyl alcohol gave 12.5 g of product; mp 152°–154°.

Anal. Calcd for $C_{17}H_{22}N_4S$: C, 64.93; H, 7.05; N, 17.82; S, 10.20.

Found: C, 64.73; H, 6.99; N, 17.65; S, 10.33.

EXAMPLE 11

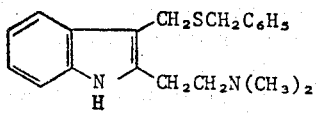

2-[2-(Dimethylamino)ethyl]-3-[(benzylthio)methyl]indole

The reaction was carried out with 2-methyl-1,2,3,4-tetrahydro-γ-carboline methiodide and benzylthiol, using work-up Method B. Recrystallization from 100 ml of isopropyl ether gave 12.4 g of product; mp 69°–72°.

Anal. Calcd for $C_{20}H_{24}N_2S$: C, 74.03; H, 7.46; N, 8.63; S, 9.88.

Found: C, 74.10; H, 7.62; N, 8.48; S, 9.88.

EXAMPLE 12

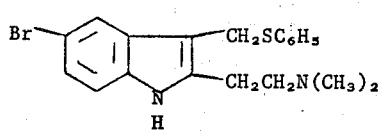

5-Bromo-2-[2-(Dimethylamino)ethyl]-3-[(phenylthio) methyl]indole

The reaction was carried out with 8-bromo-2-methyl-1,2,3,4-tetrahydro-γ-carboline methiodide and thiophenol, using work-up Method B. Recrystallization by dissolving in 600 ml of hot isopropyl ether and evaporation to a volume of 80 ml gave 19.4 g of product, mp 112°–115°.

Anal. Calcd for $C_{19}H_{21}BrN_2S$: C, 58.61; H, 5.44; Br, 20.52; N, 7.19; S, 8.23.

Found: C, 58.74; H, 5.51; Br, 20.46; N, 7.15; S, 8.26.

EXAMPLE 13

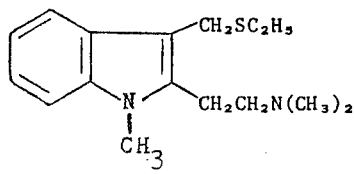

1-Methyl-2-[2-(dimethylamino)ethyl]-3-[(ethylthio) methyl]indole Hydrochloride

The reaction was carried out with 2,5-dimethyl-1,2,3,4-tetrahydro-γ-carboline methiodide and ethanethiol, using work-up Method B. Since the free base was an oil, it was redissolved in ether and treated with ethereal hydrogen chloride. Recrystallization of the crude hydrochloride from 300 ml of isopropyl alcohol gave 5.7 g of material, mp 188°–190° dec.

Anal. Calcd for $C_{16}H_{24}N_2S \cdot HCl$: C, 61.42; H, 8.05; Cl, 10.25; N, 8.95; S, 11.33.

Found: C, 61.65; H, 8.33; Cl, 10.18; N, 8.73; S, 11.28.

EXAMPLE 14

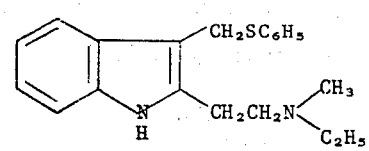

2-[2-(Ethylmethylamino)ethyl]-3-[(phenylthio)methyl]indole

The reaction was carried out with 2-methyl-1,2,3,4-tetrahydro-γ-carboline ethiodide and thiophenol, using work-up Method B. Recrystallizataion from 200 ml of cyclohexane gave 16 g of product, mp 77°–79°.

Anal. Calcd for $C_{20}H_{24}N_2S$: C, 74.03; H, 7.46; N, 8.63; S, 9.88.

Found: C, 74.16; H, 7.52; N, 8.70; S, 10.06.

EXAMPLE 15

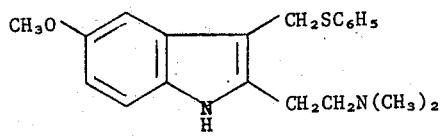

5-Methoxy-2-[2-(dimethylamino)ethyl]-3-[(phenylthio) methyl]indole

The reaction was carried out with 8-methoxy-2-methyl-1,2,3,4-tetrahydro-γ-carboline methiodide and thiophenol, using work-up Method B, except that the crude oily solid was taken up in ethyl acetate rather than ether. Evaporation gave an oil which solidified on refrigeration. Recrystallization by dissolving in 600 ml of hot isopropyl ether and concentration to a volume of 70 ml gave 11.6 g of product, mp 85°–88°.

Anal. Calcd for $C_{20}H_{24}N_2OS$: C, 70.55; H, 7.10; N, 8.23; S, 9.42.

Found: C, 70.37; H, 7.18; N, 8.46; S, 9.49.

EXAMPLE 16

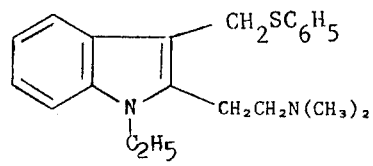

1-Ethyl-2-[2-(dimethylamino)ethyl]-3-[(phenylthio)methyl]indole Hydrochloride

The reaction was carried out with 5-ethyl-2-methyl-1,2,3,4-tetrahydro-γ-carboline methiodide and thiophenol, using work-up Method B. Since the free base was an oil, it was dissolved in ether and treated with ethereal hydrogen chloride. The crude hydrochloride was recrystallized from 120 ml of isopropanol to give 7.0 g of product, mp 148°–150°.

Anal. Calcd for $C_{21}H_{26}N_2S \cdot HCl$: C, 67.27; H, 7.26; Cl, 9.45; N, 7.47; S, 8.55.

Found: C, 67.03; H, 7.49; Cl, 9.47; N, 7.25; S, 8.70.

EXAMPLE 17

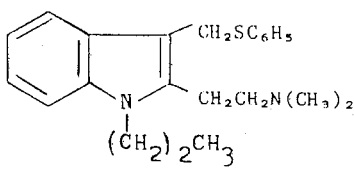

1-n-Propyl-2-[2-(dimethylamino)ethyl]-3-[(phenylthio)methyl]indole hydrochloride The reaction was carried out with 5-n-propyl-2-methyl-1,2,3,4-tetrahydro-γ-carboline methiodide and thiophenol, using work-up Method B. The free base was a tan oil. This was dissolved in ether and treated with ethereal hydrogen chloride. The resulting crude hydrochloride was recrystallized from 200 ml of isopropyl alcohol to give 13 g of product mp 141°–143°.

Anal. Calcd for $C_{22}H_{28}N_2S \cdot HCl$: C, 67.93; H, 7.51; Cl, 9.11; N, 7.20; S, 8.24.

Found: C, 68.17; H, 7.64; Cl, 9.35; N, 7.27; S, 8.11.

EXAMPLE 18

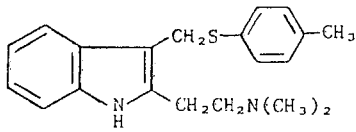

2-[2-(Dimethylamino)ethyl]-3-[p-tolylthio)methyl]indole

The reaction was carried out with 2-methyl-1,2,3,4-tetrahydro-γ-carboline methiodide and p-cresol, using work-up Method B. Recrystallization from 100 ml of hexane gave 19.7 g of product, mp 84°–87°.

Anal. Calcd for $C_{20}H_{24}N_2S$: C, 74.03; H, 7.46; N, 8.63; S, 9.88.

Found: C, 74.01; H, 7.59; N, 8.55; S, 10.12.

EXAMPLE 19

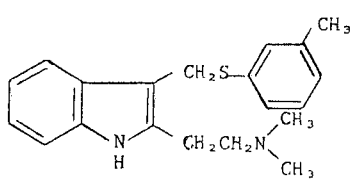

2-[2-(Dimethylamino)ethyl]-3-[(m-tolylthio)methyl]indole

The reaction was carried out with 2-methyl-1,2,3,4-tetrahydro-γ-carboline methiodide and m-cresol, using work-up Method B. Recrystallization from 60 ml of hexane gave 18.7 g of product, mp 75°–78°.

Anal. Calcd for $C_{20}H_{24}N_2S$: C, 74.03; H, 7.46; N, 8.63; S, 9.88.

Found: C, 73.90; H, 7.41; N, 8.50; S, 9.99.

EXAMPLE 20

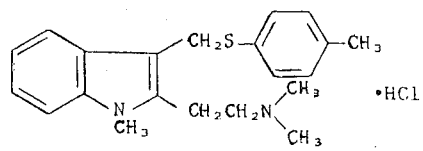

2-[2-(Dimethylamino)ethyl]-1-methyl-3-[(p-tolylthio)methyl]indole, Hydrochloride The reaction was carried out with 2,5-dimethyl-1,2,3,4-tetrahydro-γ-carboline methiodide and p-cresol, using work-up Method B. The residue obtained on evaporation of the ether extraction solvent was redissolved in ether and treated with ethereal hydrogen chloride. The crude hydrochloride salt which precipitated was collected and recrystallized from ispropyl alcohol to give 18.9 g of product, mp 162°–163°.

Anal. Calcd for $C_{21}H_{26}N_2S \cdot HCl$: C, 67.27; H, 7.26; Cl, 9.45; N, 7.47; S, 8.55.

Found: C, 67.18; H, 7.30; Cl, 9.39; N, 7.56; S, 8.80.

EXAMPLE 21

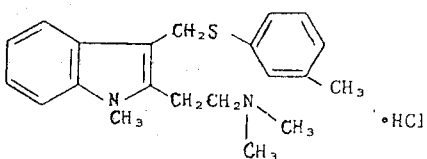

2-[2-(Dimethylamino)ethyl]-1-methyl-3-[m-tolylthio)methyl]indole, Hydrochloride

The reaction was carried out with 2,5-dimethyl-1,2,3,4-tetrahydro-γ-carboline methiodide and m-cresol, using work-up Method B. The residue obtained on evaporation of the ether extraction solvent was redissolved in ether and treated with ethereal hydrogen chloride. The resulting crude hydrochloride salt was recrystallized from isopropyl alcohol to give 17.5 g of product, mp 177°–179°.

Anal. Calcd for $C_{21}H_{26}N_2S \cdot HCl$: C, 67.27; H, 7.26; Cl, 9.45; N, 7.47; S, 8.55.

Found: C, 67.09; H, 7.30; Cl, 9.35; N, 7.45; S, 8.66.

We claim:

1. A compound of the formula

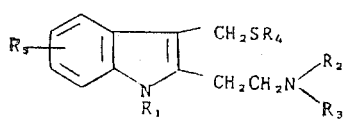

wherein $R_1$, $R_2$ and $R_3$ are hydrogen or alkyl having 1 to 7 carbon atoms, $R_4$ is alkyl having 1 to 7 carbon atoms, aryl having 6 to 10 carbon atoms, aralkyl in which aryl and alkyl are as defined, or a 5 or 6-membered heterocyclic ring having one or two atoms selected from the group consisting of nitrogen, oxygen or sulfur and $R_5$ is hydrogen, alkyl having 1 to 7 carbon atoms, alkoxy having 1 to 7 carbon atoms, and hydroxyl and the corresponding pharmaceutically acceptable acid addition salt.

2. A compound according to claim 1 which is 2[2-(dimethylamino) ethyl]-3-[(ethylthio)methyl]indole.

3. A compound according to claim 1 which is 2[2-(dimethylamino) ethyl]-3-[(phenylthio)methyl]indole.

4. A compound according to claim 1 which is 1-methyl-2-[2-(dimethylamino)ethyl]-3-[(phenylthio)methyl]indole.

5. A compound according to claim 1 which is 2-[2-(dimethylamino) ethyl]-3-[(p-chlorophenylthio)methyl]indole.

6. A compound according to claim 1 which is 2-[2-(dimethylamino) ethyl]-3-[2-(dimethylamino)ethylthiomethyl]-indole.

7. A compound according to claim 1 which is 2-[2-(dimethylamino) ethyl]-3-[(2-thiazolin-2-ylthio)methyl]indole.

8. A compound according to claim 1 which is 2-[2-(dimethylamino) ethyl]-3-[(o-tolylthio)methyl]indole.

9. A compound according to claim 1 which is 2-[2-(dimethylamino) ethyl]-3-[(2-furylmethylthio)methyl]indole.

10. A compound according to claim 1 which is 2-[2-(dimethylamino) ethyl]-3-[(1-methylimidazol-2-ylthio)methyl]indole.

11. A compound according to claim 1 which is 2-[2-(dimethylamino) ethyl]-3-[(benzylthio)methyl]indole.

12. A compound according to claim 1 which is 5-bromo-2-[2-(dimethylamino)ethyl]-3-[(phenylthio)methyl]indole.

13. A compound according to claim 1 which is 1-methyl-2-[2-(dimethylamino)ethyl]-3-[(ethylthio)methyl]indole.

14. A compound according to claim 1 which is 2-[2-(ethylmethylamino)ethyl]-3-[(phenylthio)methyl]indole.

15. A compound according to claim 1 which is 5-methoxy-2-[2-(dimethylamino)ethyl]-3-[(phenylthio)methyl]indole.

16. A compound according to claim 1 which is 1-ethyl-2-[2-(dimethylamino)ethyl]-3-[(phenylthio)methyl]indole.

17. A compound according to claim 1 which is 1-n-propyl-2-[2-(dimethylamino)ethyl]-3-[(phenylthio)methyl]indole.

18. A compound according to claim 1 which is 2-[2-(Dimethylamino) ethyl]-3-[p-tolylthiomethyl]indole.

19. A compound according to claim 1 which is 2-[2-(Dimethylamino) ethyl]-3-[(m-tolylthio)methyl]indole.

20. A compound according to claim 1 which is 2-[2-(Dimethylamino) ethyl]-1-methyl-3-[(p-tolylthio)methyl]indole.

21. A compound according to claim 1 which is 2-[2-(Dimethylamino) ethyl]-1-methyl-3-[m-tolylthio)methyl]indole.

22. A process for the production of a compound according to claim 1 which comprises refluxing a compound of the formula

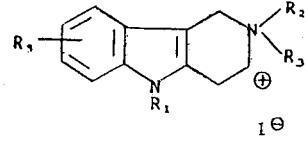

with a compound of the formula
$R_4S^-Na^+$
in which $R_1$, $R_2$, $R_3$, $R_4$ and $R_5$ are as defined in claim 1.

* * * * *